United States Patent [19]
Andersen et al.

[11] Patent Number: 5,607,394
[45] Date of Patent: Mar. 4, 1997

[54] DILATATION CATHETER HAVING A FIELD STYLET

[75] Inventors: Erik Andersen, Jyllinge; Ib Jorgensen, Ringsted, both of Denmark

[73] Assignee: Boston Scientific Corp., Natick, Mass.

[21] Appl. No.: 519,626

[22] Filed: Aug. 25, 1995

Related U.S. Application Data

[63] Continuation of Ser. No. 133,528, Oct. 7, 1993, abandoned.

[51] Int. Cl.$^6$ .................................................. A61M 29/00
[52] U.S. Cl. .......................... 604/102; 604/96; 606/194
[58] Field of Search ............................. 604/96, 102, 280, 604/282; 606/192, 194; 128/656–658

[56] References Cited

U.S. PATENT DOCUMENTS

| | | |
|---|---|---|
| Re. 34,564 | 3/1994 | Mar et al. . |
| 4,323,071 | 4/1982 | Simpson et al. . |
| 4,748,982 | 6/1988 | Horzewski et al. . |
| 4,762,129 | 8/1988 | Bonzel . |
| 4,771,777 | 9/1988 | Horzewski et al. . |
| 4,877,031 | 10/1989 | Conway et al. . |
| 4,943,278 | 7/1990 | Enteneuer et al. . |
| 4,988,356 | 1/1991 | Crittenden et al. . |
| 5,024,234 | 6/1991 | Leary et al. . |
| 5,032,113 | 7/1991 | Burns . |
| 5,040,548 | 8/1991 | Yock . |
| 5,061,267 | 10/1991 | Zeiher . |
| 5,061,273 | 10/1991 | Yock . |
| 5,090,958 | 2/1992 | Sahota . |
| 5,154,725 | 10/1992 | Leopold . |
| 5,156,594 | 10/1992 | Keith . |
| 5,171,222 | 12/1992 | Euteneuer et al. . |
| 5,180,367 | 1/1993 | Kontos et al. . |
| 5,195,971 | 3/1993 | Sirhan .................................. 604/96 |
| 5,201,316 | 4/1993 | Pomeranz et al. . |
| 5,217,482 | 6/1993 | Keith .................................. 606/194 |
| 5,232,445 | 8/1993 | Bonzel .................................. 604/96 |
| 5,242,396 | 9/1993 | Evard . |
| 5,263,928 | 11/1993 | Trauthen et al. .................... 604/53 |
| 5,263,932 | 11/1993 | Jang .................................. 604/96 |
| 5,279,562 | 1/1994 | Sirhan et al. ...................... 604/96 |
| 5,281,203 | 1/1994 | Ressemann ...................... 604/164 |
| 5,324,269 | 6/1994 | Miraki . |
| 5,328,472 | 7/1994 | Steinke et al. .................... 604/102 |
| 5,330,499 | 7/1994 | Kanesaka . |

FOREIGN PATENT DOCUMENTS

| | | |
|---|---|---|
| 2035851 | 8/1991 | Canada . |
| 0518205A1 | 12/1992 | European Pat. Off. . |
| WO89/07958 | 9/1989 | WIPO . |
| WO92/17236 | 10/1992 | WIPO . |
| WO93/05841 | 4/1993 | WIPO . |
| WO94/04216 | 3/1994 | WIPO . |

OTHER PUBLICATIONS

Cordis, Europass™ Brochure, May 1993.

*Primary Examiner*—Corrine M. McDermott
*Attorney, Agent, or Firm*—Fish & Richardson P.C.

[57] ABSTRACT

The invention features a catheter having a stylet that increases columnar strength and axial force transmission ("pushability") of the catheter shaft. This aspect of the invention features the stylet extending distally beyond an exit port which is used in rapid catheter exchange and being embedded in the catheter shaft, there being a stress-transferring relationship between the exterior of the stylet and the substance defining the shaft at least in the vicinity of the exit port, the stylet with the embedded relationship increasing the columnar strength of the shaft in the region of the port and increasing the pushability of the catheter.

18 Claims, 2 Drawing Sheets

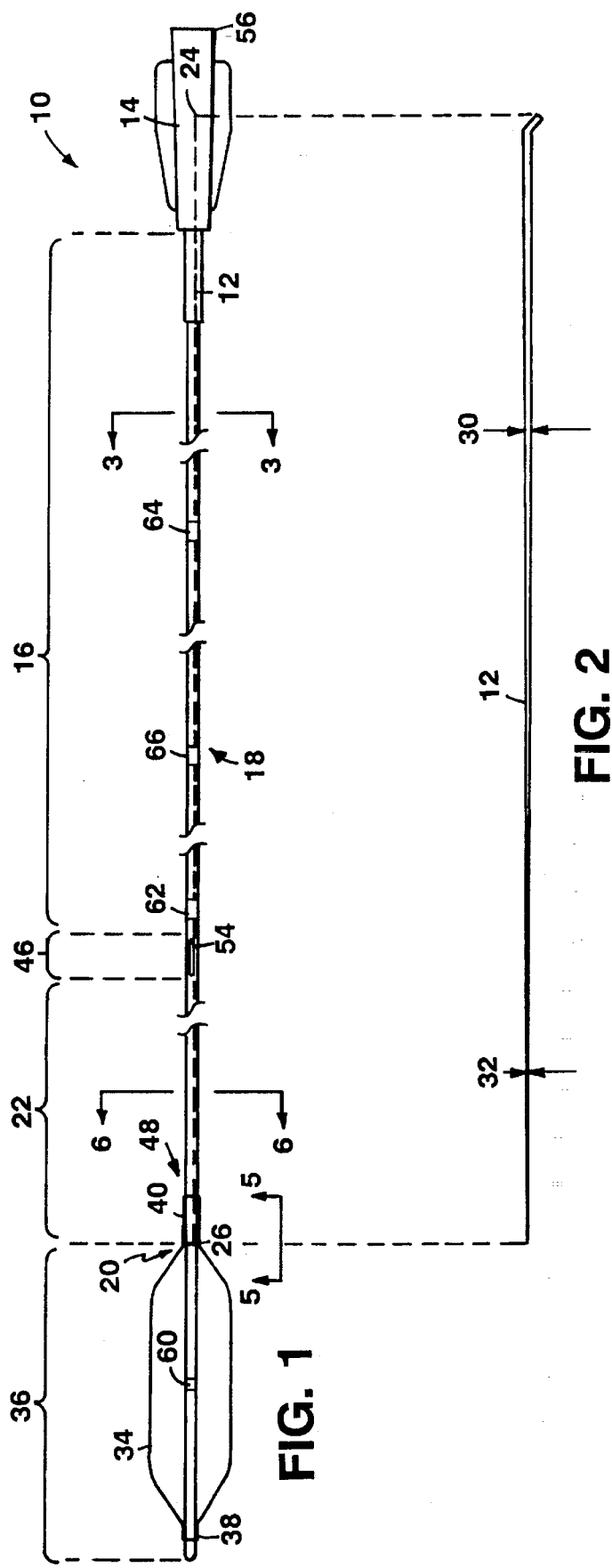
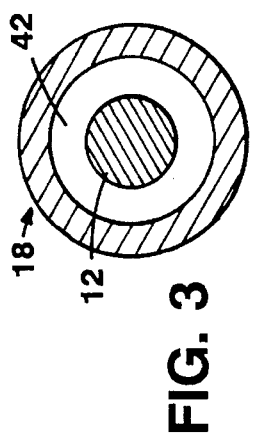
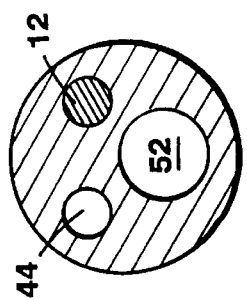

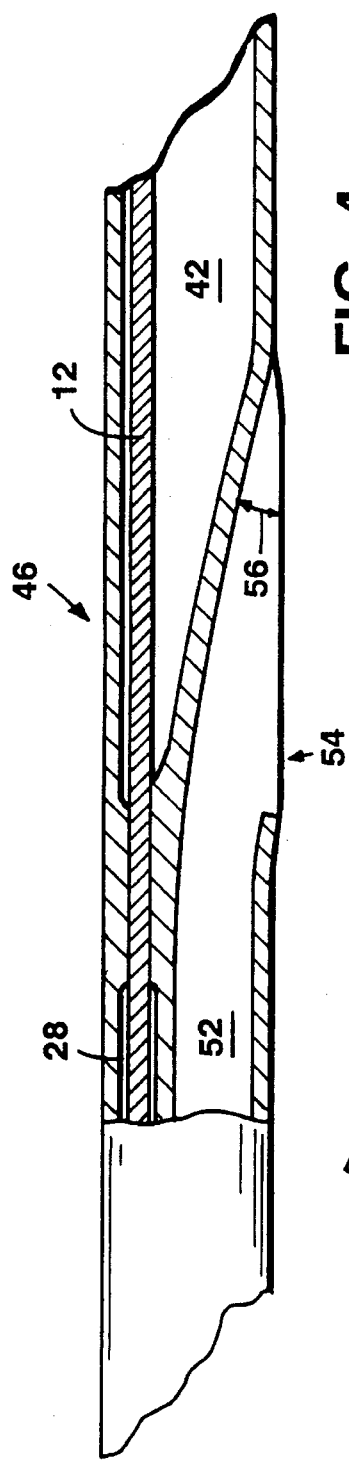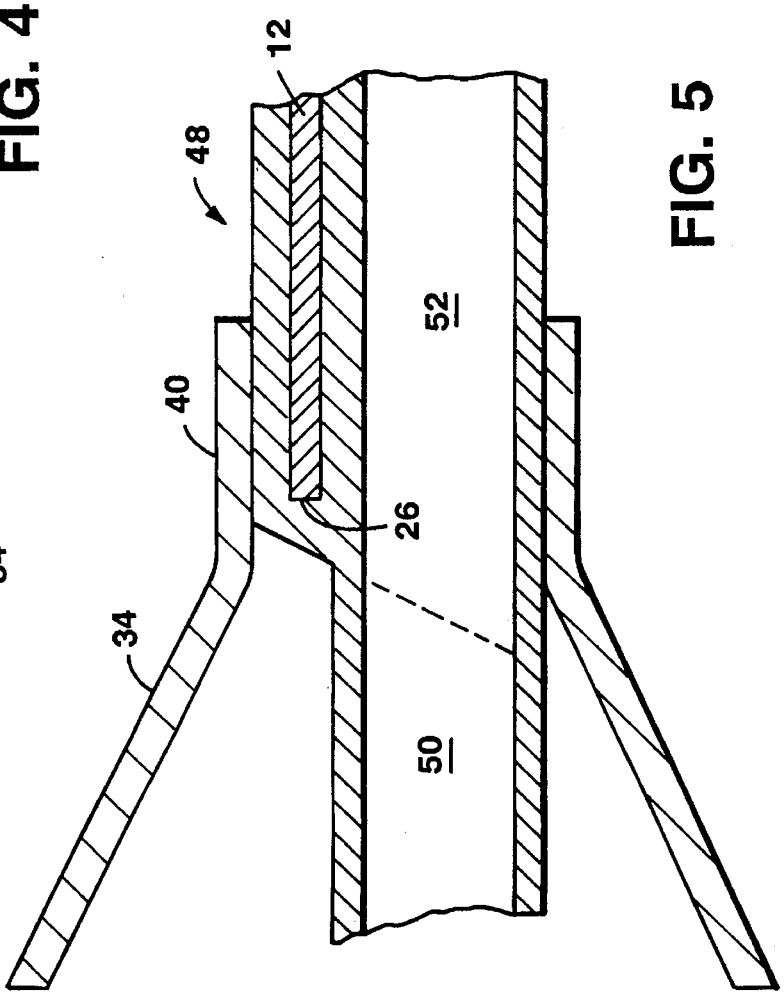

DILATATION CATHETER HAVING A FIELD STYLET

This is a continuation of application Ser. No. 08/133,528, filed Oct. 7, 1993, now abandoned.

BACKGROUND

This invention relates to dilatation catheters suitable for percutaneous transluminal coronary angioplasty (PTCA).

During a PTCA procedure, it is often necessary to exchange one dilation catheter for another. In doing so, exchange wires with lengths of up to 300 cm have been used, typically requiring the cooperation of two operators to manipulate.

To overcome certain difficulties associated with using long exchange wires, rapid exchange catheters have been developed. A rapid exchange catheter generally has a short guidewire-receiving sleeve or inner lumen extending through the distal segment of the catheter. This structure allows for the rapid exchange of the catheter.

SUMMARY

In one aspect, the invention features a catheter having a stylet that increases columnar strength and axial force transmission ("pushability") of the catheter shaft. This aspect concerns a dilatation catheter construction comprising a catheter shaft sized and constructed to enter the body of a patient via a puncture, to pass through the arterial system, and to enter a coronary artery, a dilatation balloon disposed on a distal portion of the catheter shaft, the catheter shaft being constructed to enable inflation and deflation of the balloon, a stylet extending longitudinally from a proximal region of the catheter shaft to a distal region of said catheter shaft, and a guidewire passage extending from the distal end of the catheter shaft to an exit port in the wall of the shaft, the exit port being located proximal of the balloon and substantially distal of the proximal end of the catheter shaft to facilitate rapid catheter exchange. This aspect of the invention features the stylet extending distally beyond the exit port and being embedded in the catheter shaft, there being a stress-transferring relationship between the exterior of the stylet and the substance defining the shaft at least in the vicinity of the exit port, the stylet with the embedded relationship increasing the columnar strength of the shaft in the region of the port and increasing the pushability of the catheter.

The location at which the stylet is embedded in the catheter shaft preferably includes a region in the vicinity of the exit port immediately adjacent to and distal of the exit port. A proximal end of the stylet is preferably embedded in a hub member comprising a proximal portion of the catheter. The distal end of the stylet preferably terminates in the vicinity of the proximal end of the balloon, and the distal end of the stylet is preferably embedded in the catheter shaft. The stylet preferably has a tapered outer diameter characterized in that the proximal section of the stylet has a larger outer diameter than the distal section of the stylet.

Another aspect of the invention features a PTCA catheter having a single lumen in a proximal portion which has a multi-lumen distal portion that provides a desirably large cross-sectional area for inflation and deflation of a dilatation balloon mounted on a distal segment of the catheter shaft which achieves a rapid catheter exchange capability. This aspect of the invention likewise concerns a dilatation catheter construction comprising a catheter shaft constructed to enable inflation and deflation of a dilatation balloon which mounted on a distal segment of the shaft and having a proximal segment which has a lumen extending longitudinally therethrough. In this aspect the distal segment defines, in the region following the proximal segment: (a) a guidewire passage extending from the distal end of the catheter shaft to an exit port in the wall of the distal segment of the shaft, the exit port being located proximal of the balloon and distal of the proximal segment of the catheter shaft to facilitate rapid catheter exchange; (b) a first lumen coupling with the lumen of the proximal segment at the juncture of the proximal and distal segments, the first lumen having an elongated member extending therethrough; and (c) a second lumen coupling with the lumen of the first proximal segment at the juncture of the proximal and distal segments, the second lumen being constructed for carrying fluid between the proximal end of the catheter shaft and the balloon, the second lumen having a cross-sectional area sized for rapid inflation or deflation of the balloon.

A particularly important advantage of the invention is that it combines the advantages of rapid catheter exchange with the increased pushability associated with an embedded stylet, while providing maximum cross-sectional area for inflation and deflation of the dilatation balloon, thereby reducing the times required to inflate and deflate the balloon. It is highly advantageous, during an angioplasty procedure, to be able to rapidly inflate and deflate the balloon, so that a patient's blood flow can be returned to normal as quickly as possible. Because of the high inflation pressures that can be applied by the syringe, rapid inflation times can be achieved even when inflating through a relatively small diameter lumen. However, atmospheric pressure is the highest pressure available for deflation. To achieve a more rapid deflation time, a larger diameter deflation lumen must be used. By employing a transition from a single lumen extrusion in the proximal segment of the catheter shaft, to a multi-lumen extrusion in a distal segment of the shaft, the invention maximizes the diameter of the inflation/deflation lumen, while accommodating the guidewire lumen and the lumen for the stylet.

Embodiments of the invention include the following features. The distance between the exit port and the proximal end of the balloon is preferably less than 36 cm. The juncture of the proximal and distal segments of the catheter shaft is preferably in the vicinity of the exit port. The elongated member is preferably a stylet.

Other advantages and features will becomes apparent from the following description and from the claims.

DESCRIPTION

FIG. 1 is a side view of a dilatation catheter in accordance with the invention.

FIG. 2 is a side view of a stylet for use with the dilatation catheter of FIG. 1.

FIG. 3 is a cross-sectional view of the dilatation catheter of FIG. 1 taken along line 3—3.

FIG. 4 is an enlarged side view, in partial cross-section, of a portion of the shaft of the dilatation catheter of FIG. 1 in the region of transition from a single-lumen segment to a triple-lumen segment.

FIG. 5 is a cross-sectional side view of the dilatation catheter of FIG. 1 taken along line 5—5.

FIG. 6 is a cross-sectional view of the dilatation catheter of FIG. 1 taken along line 6—6.

Referring to FIG. 1, dilatation catheter 10 has a captured stylet 12 extending from a hub 14, through a 1.1 meter long, proximal, single-lumen segment 16 of a 2.9 French catheter shaft 18, to the distal end 20 of a 20 cm long three-lumen segment 22 of shaft 18. The proximal end 24 of stylet 12 is embedded in the hub, while the distal end 26 of the stylet is embedded inside a lumen 28 of segment 22 of shaft 18.

The stylet is tapered, as shown in FIG. 2, and is preferably made from metal or metal alloy (e.g., stainless steel or Nitinol). The stylet has an overall length of about 1.35 m. In section 16 of shaft 18 the stylet has an outer diameter 30 of 0.445 mm, while in section 22 of the shaft the stylet has an outer diameter 32 of 0.20 mm.

A flexible, relatively inelastic balloon 34 is preferably blow-molded from a two layer tubing comprising Selar and PET (polyethylene terapthalate), as described in U.S. Pat. No. 5,195,969 issued to Wang et al. on Mar. 23, 1993 and in U.S. Ser. No. 07/943,977 filed by Sahatjian on Sep. 11, 1993, which are assigned to the assignee of the present application, the entire disclosures of which are herein incorporated by reference. The balloon is mounted on the distal segment 36 of the catheter shaft by bonding the proximal and distal sleeves 40 and 38, respectively, of the balloon to the outside wall of the shaft. In one embodiment, the balloon has a profile of about 3 cm and a length of about 2.7 cm.

Referring to FIG. 3, proximal section 16 of shaft 18 has a single lumen 42 extending therethrough. The space between the inside wall of segment 16 of the shaft and the outside surface of the stylet is used for communicating inflation fluid (e.g., radiopaque liquid) between the hub 14 and a lumen 44 of segment 22 of the catheter shaft.

As shown in FIG. 4, there is a 5 mm transition region 46 between the single-lumen and triple-lumen sections of the shaft. During fabrication of the catheter shaft 18, the distal end of a single-lumen polyethylene tubing extrusion and the proximal end of a three-lumen polyethylene tubing extrusion are melted together inside a mold. Mandrels are inserted into the lumens of the tubes to maintain their shape during the melting procedure. The tubes melt and cause the polyester material forming the wall of lumen 28 to surround the distal end of stylet 12, thereby embedding the stylet in the distal portion 48 of segment 22. Because the stylet is embedded in the hub 14 and in the distal segment 22 of shaft 18, axial force can be directly transmitted along the stylet 12 from the hub to the distal segment. The distal end of segment 22 of the catheter shaft is similarly molded together with another extruded tubing which has a lumen 50 axially aligned with lumen 52 of segment 22 (FIG. 5).

The catheter shaft 18 has an exit port 54 disposed through the wall of the shaft and into lumen 50 of distal segment 36, as shown in FIG. 4, for slidably receiving a guidewire in rapid catheter exchange PTCA procedures. The exit port is preferably a slightly oval opening of about 3 mm long and 0.5 mm wide, arranged at an angle 56 of about 20 to 60 degrees with respect to the longitudinal axis of the catheter shaft. The exit port 54 is disposed proximally of the proximal sleeve 23 of the balloon a distance about 15 cm to about 35 cm. Lumen 50 may thus be utilized in its entire length, from the exit port to its distal end in a rapid catheter exchange procedure with a guidewire extending through lumen 50 and out the exit port 54.

In a PTCA procedure, a guidewire is advanced through a guiding catheter, into a coronary artery of a patient, and across a lesion to be dilated. The proximal end of the guidewire is inserted into the distal end of lumen 50 of the catheter shaft 18 and out through the exit port 54. The guidewire extends parallel to and external of the catheter shaft proximal of the exit port. The catheter is advanced over the guidewire to the coronary artery until the balloon is properly positioned across the lesion, at which point the balloon is inflated to a predetermined size with inflation fluid to dilate the stenosed region. The balloon is then deflated so that the dilatation catheter can be removed.

In such a PTCA procedure the guide wire may have a bend in the vicinity of the exit port near the transition region 46. The frictional forces resisting the motion of the catheter over the guidewire are increased in the area of the bend in the guide wire. Conventional catheters are typically made from nylon materials which are stiffer than polyethylene. However, polyethylene is more lubricous than nylon and thus provides less resistance to the motion of the guidewire through it.

Because stylet 12 extends longitudinally from the proximal end of the catheter shaft past the exit port, and is embedded in the catheter shaft in the vicinity of the exit port 54 in region 46 (FIG. 4), the catheter shaft has a high columnar strength (which e.g., reduces buckling), and there is good axial force transmission ("pushability") between the proximal end of the shaft and the region of increased resistance near the bend in the guidewire. Thus, the invention provides the advantage of increased axial force transmission between the proximal end of the catheter and the point of highest frictional resistance to the advancement of the catheter.

There are also situations in which the catheter must be advanced over a guidewire through a sufficiently tight stenosis that the region of greatest resistance to the advancement of the catheter is at the distal segment of the catheter. Because the stylet is embedded at the proximal sleeve 40 of the balloon 34, there is good pushability of the catheter up to the proximal end of the balloon. In a preferred embodiment the stylet does not extend beyond the proximal end of the balloon. This allows the balloon to achieve a minimal profile facilitating negotiation of the catheter through tight stenoses, and enabling the distal section 36 of the catheter to have good flexibility.

The proximal end of the hub 14 has threads 58 for coupling the dilatation catheter to a source of inflation fluid (e.g., a hand-held syringe). Lumen 42 of section 16 and lumen 44 of section 22 may be used to deliver the inflation fluid between the hub and balloon 34. A conventional syringe may inflate the balloon to a predetermined size with inflation fluid at relatively high pressures (e.g., 4–12 atmospheres) to dilate a stenosed region of a diseased artery. The syringe may deflate the balloon by creating a subambient pressure in lumens 42 and 48. The pressure inside the artery (i.e., about one atmosphere) causes the fluid to evacuate the balloon.

Because of the transition from a single lumen extrusion in the proximal segment 16 of the catheter shaft to a multi-lumen extrusion in segment 22 of the shaft, the diameter of lumen 44 is maximized, while accommodating the guidewire lumen, and the lumen for the stylet. This is due to the fact that in other design schemes (e.g., schemes in which the guide wire lumen and the inflation lumen are defined by coaxial tubes) the wall thickness required to define the inner lumen takes up cross-sectional area.

A gold radio opaque marker band 60 is disposed about the catheter shaft 18, at the midpoint of the balloon 34. A marker band 62 is disposed about the catheter shaft about 2 mm proximal to the exit port to indicate the location of the exit port to an operator. In addition, exit markers 64 and 66 are similarly disposed about the catheter shaft to indicate the position of the balloon of the dilatation catheter 10 with respect to the distal end of a guiding catheter during a PTCA procedure. In a PTCA procedure in which access to a patient's arterial system is achieved through the femoral artery, when the dilation catheter is advanced through a guiding catheter and the marker 64 is immediately adjacent the proximal end of the guiding catheter, which is about 1.05 m proximal of the balloon, the balloon will have just exited the distal end of the guiding catheter. Marker 66 is used similarly, except for the case in which access to a patient's vasculature is achieved through the arm.

Other embodiments are within the scope of the following claims:

We claim:

1. A PTCA dilatation balloon catheter comprising:

a catheter shaft having proximal and distal ends and having a length selected to access a coronary artery of a patient, said catheter shaft being sized and constructed to enter the body of a patient via a puncture, to pass through the arterial system, and to enter the coronary artery, wherein said catheter shaft has a generally tubular outer wall and defines a single-lumen proximal section that extends over the majority of the length of said catheter shaft, a multi-lumen intermediate section having multiple lumens defined by polymeric material, and a single-lumen distal section, the multi-lumen intermediate section having a guidewire exit port in the shaft wall, the exit port being located a substantial distance from the proximal end of the catheter shaft to facilitate rapid catheter exchange;

a dilatation balloon having proximal and distal ends mounted between the intermediate section and the distal section of said catheter shaft, said balloon being coupled to the proximal end of said catheter shaft through a first of the lumens of the multi-lumen intermediate section and through the single-lumen proximal section of the catheter shaft to enable inflation and deflation of said balloon;

wherein a second of the lumens of the multi-lumen intermediate section of the catheter shaft forms, together with the lumen of the distal section, a guidewire passage that extends from the distal end of said catheter shaft, through said intermediate section, to the guidewire exit port; and a fixed stylet having proximal and distal ends, said stylet extending from the vicinity of the proximal end of said catheter shaft, distally beyond said exit port through a lumen in the intermediate catheter section, and terminating at the proximal end of said balloon, the distal end of said stylet being fixedly secured to the polymeric material defining the lumen in the intermediate section of said catheter shaft in which the stylet resides, there being a stress-transferring relationship between the exterior of said stylet and the substance of the lumen of the intermediate section of said shaft in which the stylet resides, said stylet with said stress-transferring relationship contributing to the columnar strength of said shaft and increasing the pushability of said catheter.

2. The catheter of claim 1 wherein said stylet is fixedly attached to said catheter shaft at a location immediately adjacent said exit port.

3. The catheter of claim 1 wherein said stylet is fixedly coupled to said catheter shaft in the vicinity of the proximal end of said catheter shaft.

4. The catheter of claim 3 further comprising a hub attached to the proximal end of said catheter shaft, wherein the proximal end of said stylet is fixedly attached to said hub.

5. The catheter of claim 1 wherein said stylet has proximal and distal sections and a tapered outer diameter characterized in that the proximal section of said stylet has a larger outer diameter at any location along its length than the diameter at any location along the length of the distal section of said stylet.

6. The catheter of claim 1 wherein said catheter shaft is formed from a proximal single-lumen tube having a distal end and a distal tube having at least two lumens and a proximal end fixedly attached to the distal end of said proximal single-lumen tube.

7. The catheter of claim 1 wherein the distal end of said stylet is embedded in the polymeric material defining the lumen of the intermediate catheter section in which said stylet resides.

8. The catheter of claim 1 wherein, in the vicinity of the guidewire exit port, the stylet is embedded in the polymeric material of the lumen of the intermediate catheter section in which said stylet resides.

9. A PTCA dilatation balloon catheter comprising:

a catheter shaft having proximal and distal ends and having a length selected to access a coronary artery of the patient, said catheter shaft being sized and constructed to enter the body of a patient via a puncture, to pass through the arterial system, and to enter a coronary artery, wherein said catheter shaft has a generally tubular outer wall and defines a single-lumen proximal section that extends over the majority of the length of said catheter shaft, a multi-lumen intermediate section consisting of polymeric material, and a single-lumen distal section, the multi-lumen intermediate section having a guidewire exit port in the shaft wall, the exit port being located a substantial distance from the proximal end of the catheter shaft to facilitate rapid catheter exchange;

a dilatation balloon having proximal and distal ends mounted between the intermediate section and the distal section of said catheter shaft, said balloon being coupled to the proximal end of said catheter shaft through a first of the lumens of the multi-lumen intermediate section and through the single-lumen proximal section of the catheter shaft;

wherein a second of the lumens of the multi-lumen intermediate section of the catheter shaft forms, together with the lumen of the distal section, a guidewire passage that extends from the distal end of said catheter shaft, through said intermediate section, to the guidewire exit port; and a fixed stylet having proximal and distal portions terminating respectively at proximal and distal ends, said stylet extending from the vicinity of the proximal end of said catheter shaft, distally beyond said exit port, and terminating at the proximal end of said balloon, there being a stress-transferring relationship between the exterior of said stylet and the substance of said shaft at least in the vicinity of said exit port, said stylet with said stress-transferring relationship contributing to the columnar strength of said shaft in the vicinity of said guidewire exit port and increasing the pushability of said catheter, wherein said stylet is embedded in the polymeric material of the intermediate catheter section at the distal end of said stylet and in the vicinity of said exit port, and the proximal portion of said stylet is fixedly coupled to said catheter shaft in the vicinity of the proximal end of said catheter shaft.

10. A PTCA dilatation balloon catheter comprising a catheter shaft having a length selected to access a coronary artery of a patient, said shaft being sized and constructed to enter the body of the patient via a puncture, to pass through the arterial system, and to enter a coronary artery, wherein said catheter shaft has a generally tubular outer wall and defines a single-lumen proximal section that extends over the majority of the length of said catheter, a multi-lumen intermediate section, and a single-lumen distal section, said proximal, intermediate, and distal sections having respective proximal and distal ends, the multi-lumen intermediate section having a guidewire exit port in the shaft wall, the exit port being located a substantial distance from the proximal end of the catheter shaft to facilitate rapid catheter exchange, and a dilatation balloon having proximal and distal ends mounted between the intermediate and distal sections of said catheter shaft, said intermediate section defining first, second, and third non-coaxial lumens:
 (a) the first lumen being coupled to the lumen of the distal section of the catheter shaft and extending proximally from the distal end of the intermediate section of said catheter shaft, through said intermediate section, and to the guidewire exit port;
 (b) the second lumen being coupled to the single lumen of said proximal section; and
 (c) the third lumen being coupled between the balloon and the lumen of the proximal section to enable delivery of inflation fluid to said balloon; and further comprising an elongated member having proximal and distal ends that are fixedly attached to said catheter shaft, said elongated member extending distally from the vicinity of the proximal end of said proximal section, through the single lumen of said proximal section and into the second lumen of the intermediate section, distally beyond said exit port, and terminating at the proximal end of the balloon.

11. The catheter of claim 10 wherein the distance between said exit port and the proximal end of said balloon is less than 36 cm.

12. The catheter of claim 10 wherein said elongated member is a stylet.

13. The catheter of claim 12 wherein said stylet is fixedly attached to said distal section at location in the vicinity of said exit port.

14. The catheter of claim 12 wherein said stylet is fixedly attached to said catheter shaft in the vicinity of said exit port by embedding said stylet in the substance defining said catheter shaft.

15. The catheter of claim 12 further comprising a hub attached to the proximal end of said catheter shaft, wherein the proximal end of said stylet is fixedly attached to said hub.

16. The catheter of claim 12 wherein said stylet is fixedly attached to catheter shaft at a location distal of said exit port.

17. The catheter of claim 12 wherein the distal end of said stylet is fixedly attached to said catheter shaft in the vicinity of said exit port by embedding said stylet in the substance defining said catheter shaft and the proximal end of said stylet is fixedly coupled to said catheter shaft in the vicinity of the proximal end of said catheter shaft.

18. The catheter of claim 10 wherein the intermediate catheter section consists of polymeric material and the elongated member is a stylet which has a distal end that is embedded in the polymeric material of the intermediate catheter section at a location adjacent and proximal of the proximal end of the balloon.

* * * * *